US011850035B2

(12) United States Patent
Daunert et al.

(10) Patent No.: US 11,850,035 B2
(45) Date of Patent: Dec. 26, 2023

(54) BREATH ANALYSIS METHODOLOGY FOR MEDICAL DIAGNOSTICS

(71) Applicant: UNIVERSITY OF MIAMI, Miami, FL (US)

(72) Inventors: Sylvia Daunert, Miami, FL (US); Jeramy Lee Rueff Baum, Miami, FL (US); Carl Ivan Schulman, Miami, FL (US); Sapna K. Deo, Miami, FL (US); Emre Dikici, Miami, FL (US); Chitvan Killawala, Miami, FL (US); Kelly Withum, Miami, FL (US); Kevin Miller, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 342 days.

(21) Appl. No.: 15/733,998

(22) PCT Filed: Jun. 25, 2019

(86) PCT No.: PCT/US2019/038891
§ 371 (c)(1),
(2) Date: Dec. 1, 2020

(87) PCT Pub. No.: WO2020/005874
PCT Pub. Date: Jan. 2, 2020

(65) Prior Publication Data
US 2021/0228104 A1     Jul. 29, 2021

Related U.S. Application Data

(60) Provisional application No. 62/756,851, filed on Nov. 7, 2018, provisional application No. 62/689,729, filed on Jun. 25, 2018.

(51) Int. Cl.
*A61B 5/08*     (2006.01)
*G16H 40/63*     (2018.01)
(Continued)

(52) U.S. Cl.
CPC .............. *A61B 5/082* (2013.01); *A61B 5/18* (2013.01); *A61B 5/4845* (2013.01);
(Continued)

(58) Field of Classification Search
CPC ......... A61B 5/082; A61B 5/083; A61B 5/091; A61B 5/18; A61B 5/4845; A61B 5/6893;
(Continued)

(56) References Cited

U.S. PATENT DOCUMENTS 9,102,220 B2    8/2015  Breed
9,341,632 B1 *  5/2016  Ahmad ................ A61B 5/0024
(Continued)

FOREIGN PATENT DOCUMENTS

CN        103359022 B       8/2016
WO      WO-03/008928 A2     1/2003
WO      WO-2007/103474 A2   9/2007

OTHER PUBLICATIONS

King et al., Measurement of endogenous acetone and isoprene in exhaled breath during sleep, Physiol. Meas. 33(3):413-28 (Mar. 2012).
(Continued)

*Primary Examiner* — Eric F Winakur
*Assistant Examiner* — Emily C Clement
(74) *Attorney, Agent, or Firm* — MARSHALL, GERSTEIN & BORUN LLP

(57) ABSTRACT

Systems and methods for diagnosing a condition in an individual by analyzing the individual's breath are provided. Sensors may be configured to capture data associated with the breath of an individual. The data captured by the sensors may include a change in resistance measurements recorded by solid-state sensors when the sensors are exposed to the individual's breath at several different temperatures. This captured data may be analyzed to identify one or more
(Continued)

volatile organic compound (VOC) biomarkers in the individual's breath. Based on the identified VOC biomarkers, a condition associated with the individual may be determined. For example, a medical condition, or a condition of drowsiness or fatigue associated with the individual may be determined based on the VOC biomarkers in the individual's breath. In some examples, the sensors may be positioned inside a vehicle for determination of condition associated with a driver of the vehicle.

16 Claims, 20 Drawing Sheets

(51) Int. Cl.
    *A61B 5/18*     (2006.01)
    *A61B 5/00*     (2006.01)
    *G01N 33/497*     (2006.01)

(52) U.S. Cl.
    CPC ....... *A61B 5/6893* (2013.01); *G01N 33/4972* (2013.01); *G16H 40/63* (2018.01); *A61B 2503/22* (2013.01); *A61B 2562/04* (2013.01); *G01N 2033/4975* (2013.01)

(58) Field of Classification Search
    CPC ............ A61B 2503/22; A61B 2562/04; A61B 5/7246; G01N 33/4972; G01N 2033/4975; G01N 33/497; G16H 40/63; G16H 50/20; B60W 2040/0836; G08B 21/06

See application file for complete search history.

(56) References Cited

U.S. PATENT DOCUMENTS

| | | | |
|---|---|---|---|
| 9,368,014 B1* | 6/2016 | Bittman | G08B 25/08 |
| 9,956,963 B2 | 5/2018 | Vijaya Kumar et al. | |
| 10,709,388 B2 | 7/2020 | Goldstein | |
| 2014/0334653 A1 | 11/2014 | Luna et al. | |
| 2014/0366610 A1* | 12/2014 | Rodriguez | G01N 33/497 |
| | | | 73/23.3 |
| 2015/0126824 A1 | 5/2015 | LeBoeuf et al. | |
| 2015/0294086 A1 | 10/2015 | Kare et al. | |
| 2017/0127976 A1 | 5/2017 | Phillips | |
| 2017/0227508 A1* | 8/2017 | Cai | G01N 33/497 |
| 2018/0038825 A1* | 2/2018 | Ratto | G01N 33/497 |
| 2018/0074030 A1* | 3/2018 | DeVries | G01N 33/4972 |
| 2019/0271685 A1* | 9/2019 | Haick | G01N 33/497 |

OTHER PUBLICATIONS

International Application No. PCT/2019/038891, International Search Report and Written Opinion, dated Aug. 30, 2019.

* cited by examiner

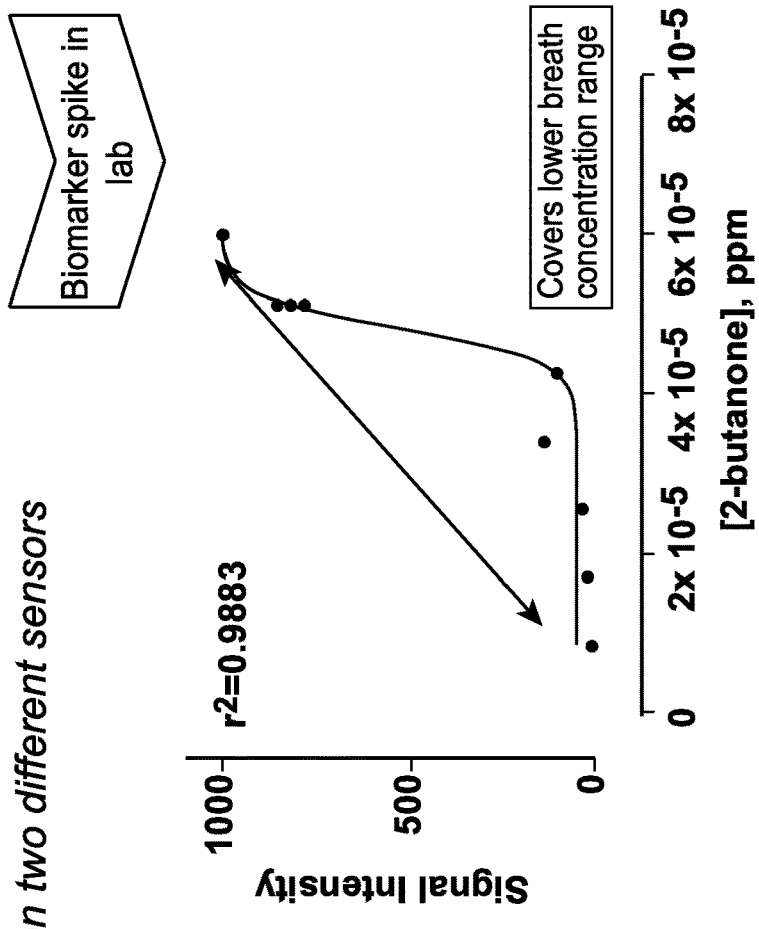
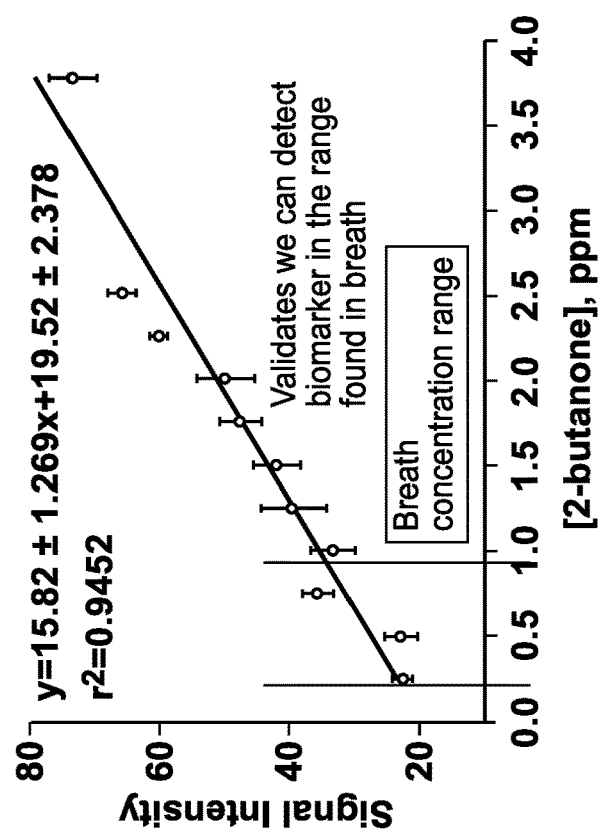
FIG. 2B
FIG. 2A

| Biomarker Detection ||
|---|---|
| Validated Biomarkers | Potential New Biomarkers |
| 2-ethyl-1-hexanol | 2-methylbutane |
| 2-ethoxyethanol | 1,4-dioxane |
| Phenol | 4-methyl-1-pentanol |
| 2-butanone | 2--methyl-2-butenal |
| Branched long-chain hydrocarbons | 4-methyloctane |

FIG. 15

BREATH ANALYSIS METHODOLOGY FOR MEDICAL DIAGNOSTICS

CROSS-REFERENCE TO RELATED APPLICATIONS

This application claims priority to provisional U.S. Application Ser. No. 62/756,851, filed on Nov. 7, 2018 and to provisional U.S. Application Ser. No. 62/689,729, filed on Jun. 25, 2018, the entire disclosures of each of which are hereby expressly incorporated by reference herein.

FIELD OF THE DISCLOSURE

The present disclosure generally relates to detecting a condition in an individual and, more particularly, to detecting a condition in an individual by analyzing the individual's breath.

BACKGROUND

Operation of a vehicle while sleep-deprived, drowsy, or in otherwise adverse physiological condition is conventionally understood to lead to greater risk of accidents. This results in approximately 5,000 fatalities and costs upwards of $100 billion in damages from fatigue-related crashes annually.

SUMMARY

In one aspect, a method for detecting a condition in an individual by analyzing the individual's breath is provided. The method comprises: capturing, by one or more sensors, data associated with the breath of an individual, analyzing, by a processor, the data captured by the one or more sensors to identify one or more volatile organic compound biomarkers, and determining, by the processor, based on the identified one or more volatile organic compound biomarkers, a condition associated with the individual.

In another aspect, a system for detecting a condition in an individual by analyzing the individual's breath is provided. The system comprises: one or more sensors configured to capture data associated with the breath of an individual, a memory configured to store computer executable instructions; and at least one processor configured to interface with the one or more sensors and the memory. The processor is configured to execute the computer executable instructions to cause the at least one processor to: analyze the data captured by the one or more sensors to identify one or more volatile organic compound biomarkers and determine, based on the identified one or more volatile organic compound biomarkers, a condition associated with the individual. In some instances, one or more of these processing steps may be performed, at least in part, via cloud computing.

BRIEF DESCRIPTION OF THE DRAWINGS

FIG. 2A illustrates the upper bounds of the concentration of VOC biomarkers found in breath as published in literature.

FIG. 2B illustrates the concentrations of VOCs that solid-state sensors are capable of detecting in a laboratory environment, in accordance with an embodiment.

FIG. 15 illustrates a table of various biomarkers identified using SPME fibers and GC-MS during the study of FIG. 14, in accordance with an embodiment.

DETAILED DESCRIPTION

As discussed above, operation of a vehicle while sleep-deprived, drowsy, or in otherwise adverse physiological condition is conventionally understood to lead to greater risk of accidents. This results in approximately 5,000 fatalities and costs upwards of $100 billion in damages from fatigue-related crashes annually.

Systems and methods for diagnosing a condition in an individual by analyzing the individual's breath are provided herein. Sensors may be configured to capture data associated with the breath of an individual. The data captured by the sensors may include a change in resistance measurements recorded by solid-state sensors when the sensors are exposed to the individual's breath at several different temperatures. This captured data may be analyzed to identify one or more volatile organic compound (VOC) biomarkers in the individual's breath. Based on the identified VOC biomarkers, a condition associated with the individual may be determined. For example, a medical condition, or a condition of drowsiness or fatigue associated with the individual may be determined based on the VOC biomarkers in the individual's breath. Additionally, the presence of alcohol, or gases such as $CO_2$ or $H_2$, may be detected using these sensors. In some examples, the sensors may be positioned inside a vehicle for determination of condition associated with a driver of the vehicle.

Figure 1:
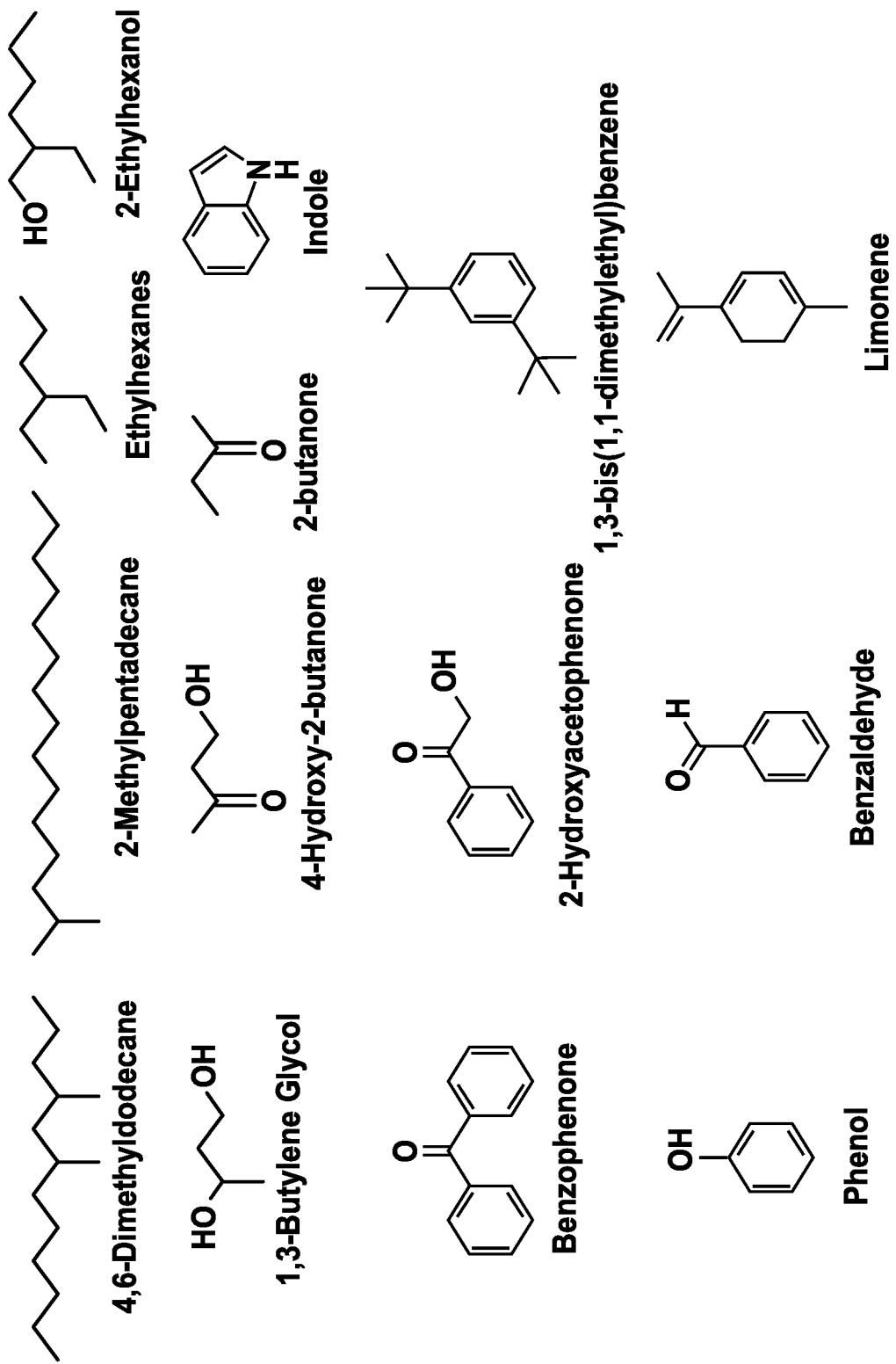
FIG. 1 illustrates several volatile organic compound (VOC) biomarkers associated with drowsiness and fatigue, in accordance with an embodiment.

Breath analysis is a favorable analytical technique for noninvasive monitoring of VOC biomarkers that indicate drowsiness and fatigue. As shown in FIG. 1, VOC biomarkers that indicate drowsiness and fatigue may include, for instance, 2-Butanone, 4,6-Dimethyldodecane, 2-Methylpentadecane, Ethylhexanes, 2-Ethylhexanol, 1,3-Butylene Glycol, 4-Hydroxy-2-Butanone, Indole, Benzophenone, Hydroxyacetophenone, 1,3-bis(1,1-dimethylethyl)benzene, Phenol, Benzaldehyde, and/or Limonene. In addition, breath analysis is very suitable as a medical diagnostic tool. In one example, solid-state sensors, combined with chemometric analysis, may be utilized to non-invasively detect VOC biomarkers in the breath correlating with drowsiness. This technology may be further expanded to detect VOC biomarkers associated with various other health/medical conditions such as acute kidney failure, diabetes, various bacterial lung infections, the onset of a heart attack, etc.

Figure 3:
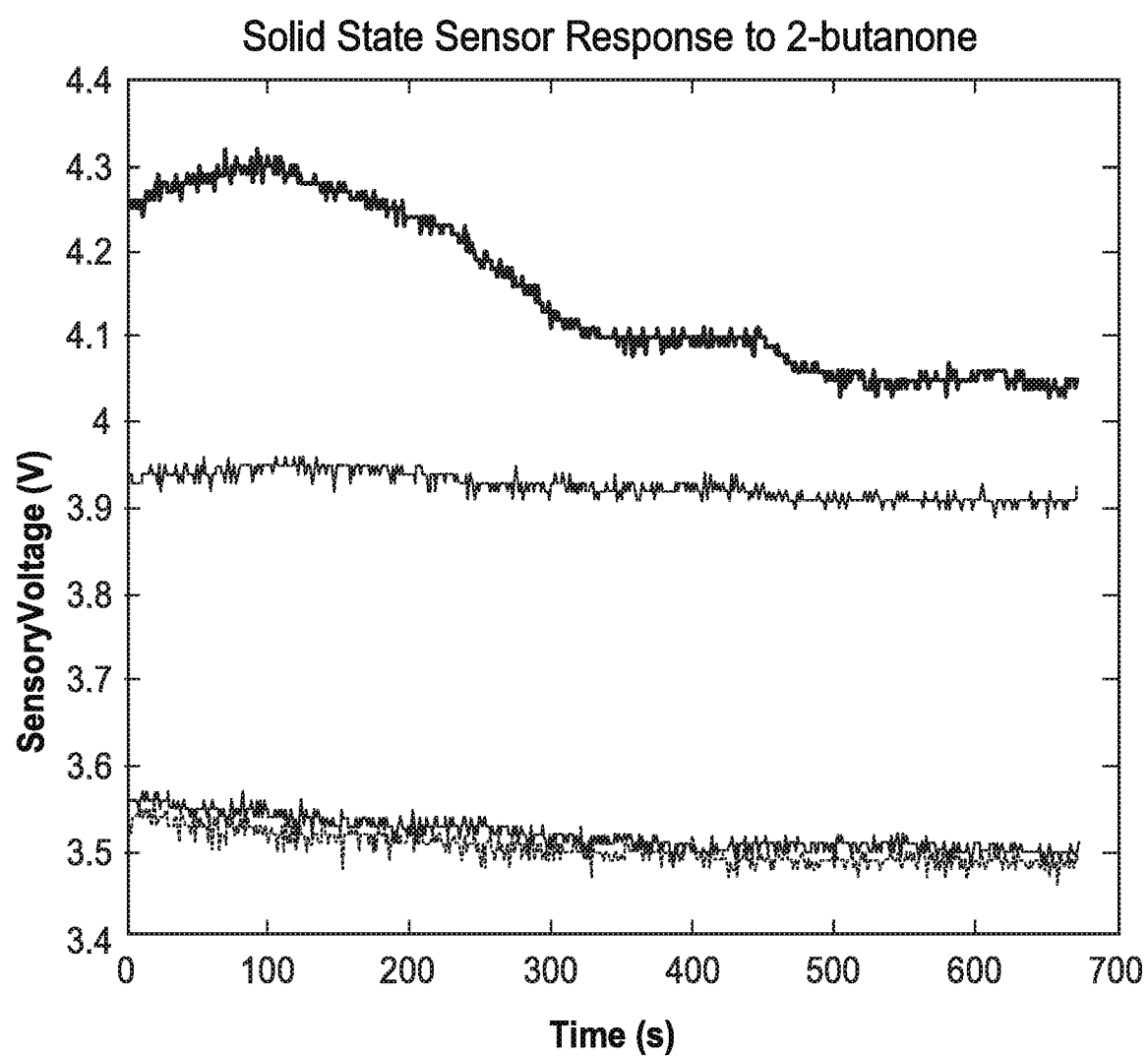
FIG. 3 illustrates the concentration of an exemplary VOC detected by solid-state sensors within the interior of an automobile, in accordance with an embodiment.

Advantageously, solid-state sensors are compact, portable, room-temperature operable, user-friendly, highly sensitive, safe, robust, precise, accurate, capable of real-time measurement, and inexpensive. Furthermore, solid-state sensors are capable of detecting minute quantities of different biomarkers in both a controlled laboratory environment as well as in the interior of an automobile. For example, as shown in FIG. 2A, the upper bounds of the concentration of VOC biomarkers found in breath as published in literature are noted to fall within the range of 200 to 500 parts per billion (ppb). As shown in FIG. 2B, solid-state sensors are capable of detecting very low concentrations, to a sub 0.5 ppb level, in a laboratory environment. Moreover, as shown in FIG. 3, a low concentration of a VOC such as 2-butanone may be detected by various solid-state sensors within the interior of an automobile.

Figure 4:
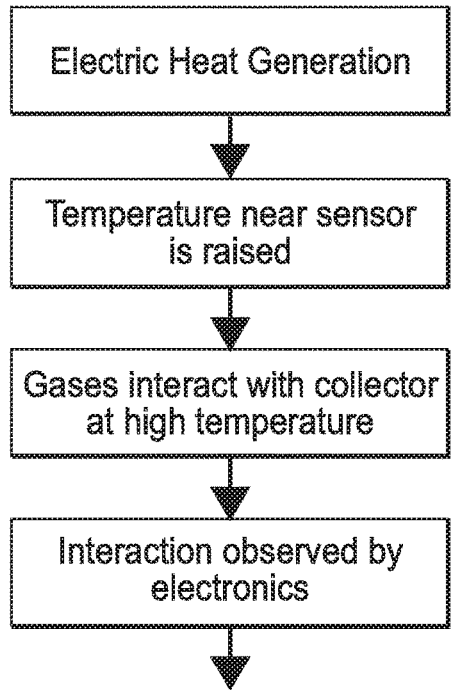
FIG. 4 illustrates the functioning of an exemplary solid-state sensor, in accordance with an embodiment.
Figure 4:
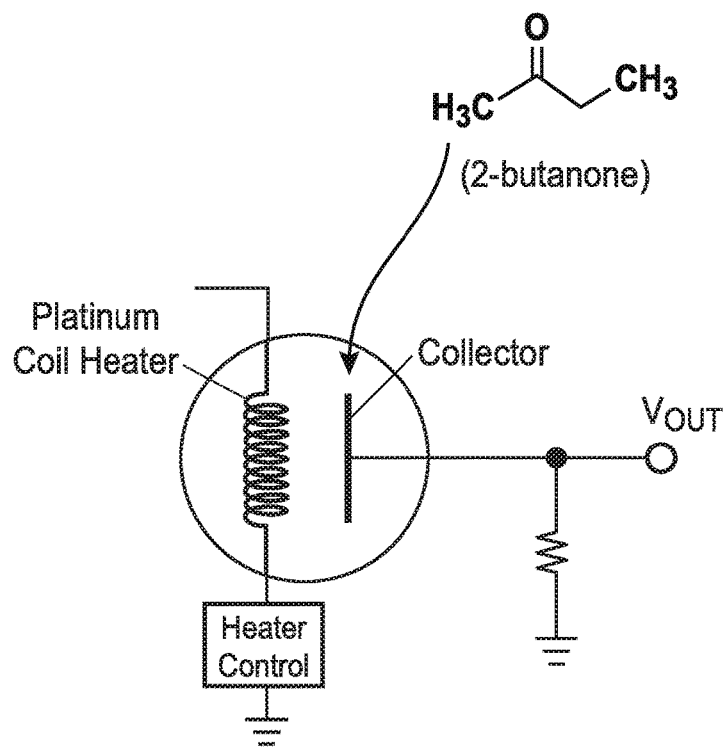

Generally speaking, solid-state sensors function as shown in FIG. 4. An electric heater raises the temperature of the area surrounding the sensor, and gases such as VOCs accordingly interact with the sensor at higher temperatures. Consequently, the interaction between the sensor and the VOC is recorded as a change in resistance. Accordingly, a change in resistance may indicate the presence of a VOC in the area of the solid-state sensor.

Figure 5A:
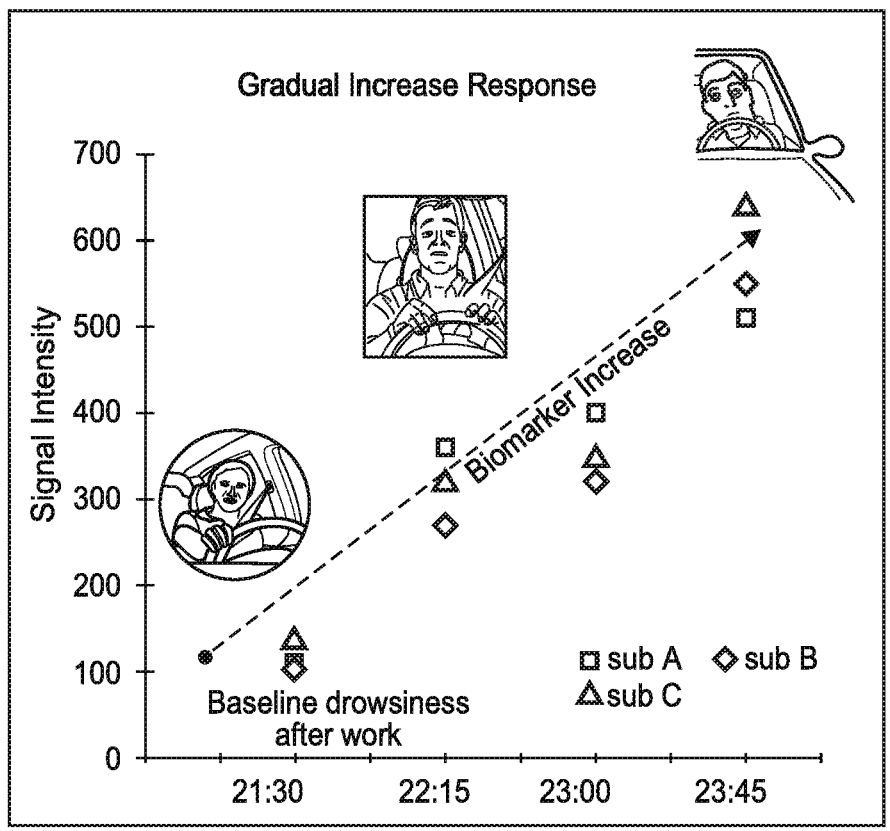
FIG. 5A illustrates a solid-state sensor responding gradually to the detection of a VOC biomarker present in the air, in accordance with an embodiment.
Figure 5B:
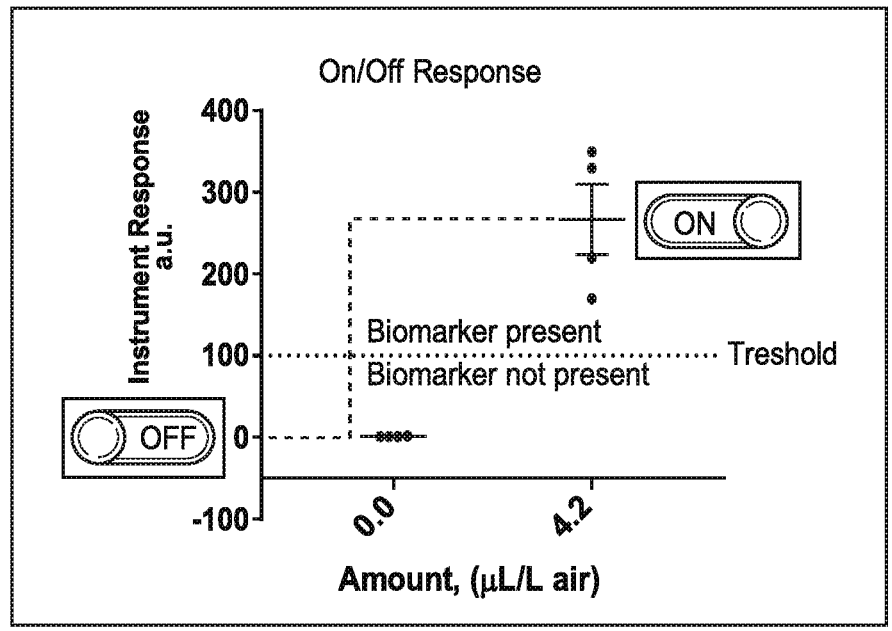
FIG. 5B illustrates a solid-state sensor responding suddenly once a certain threshold concentration of a VOC biomarker is present in the air, in accordance with an embodiment.

However, a single sensor alone may not be very selective to a specific VOC biomarker, and a molecule with a similar structure may also cause the sensor to respond. Moreover, as shown in FIGS. 5A and 5B, two types of solid-state sensors may be manufactured differently, with one type (as shown in FIG. 5A) responding with gradual detection increase and the other type (as shown in FIG. 5B) responding suddenly once a certain threshold concentration of a certain biomarker is present in the air. The advantage of using a sensor that is capable of a gradual increase response is that it can be used to give an approximation of the concentration of the compound it detects in the surrounding environment, whereas the advantage of using a sensor that adopts an on-off response paradigm is the fact that it can be used to create a simple alert system once a concentration threshold is reached.

Advantageously, a sensor array including multiple solid-state sensors calibrated to different situations may be utilized to ensure that various biomarkers related to a given condition can all be detected. That is, a solid-state sensor array, in addition to the aforementioned benefits of single solid-state sensors, is capable of detecting multiple biomarkers in parallel. For example, an Arduino microcontroller may control a heater voltage and read sensor resistance values corresponding to each biomarker signal. The use of a sensor array rather than a single sensor in further improves the analysis and predictive abilities of the technology described herein, as it is already understood that these sensors will respond to other groups of compounds in addition to the intended compound. The concept of using sensors in an array gives additional selectivity using calibration curves and the software to detect the presence of various compounds. Data profiles for the sensor arrays to work may be developed, including the types of sensors and their properties as well as integration of the information from the various sensors. Various chemometric analyses may be utilized to filter the multidimensional datasets using techniques related to multivariate analysis and principle component analysis. In some instances, machine-learning techniques may be incorporated to improve the confidence of the datasets. In some instances, sensors may be made, using various fabrication techniques, with novel materials such as graphene and carbon nanotubes in addition to regular semiconductors to increase the scope of detection. Moreover, the use of electrical fields and electrical potentials may increase the data variety and alter the way various biomarkers will respond to the sensor.

One exemplary sensor array includes five solid-state sensors, but any number of solid-state sensors may be included in various embodiments. Responses at various heater voltages may be observed for a multidimensional dataset. Using the change in resistance of the sensor as an indicator, calibration curves may be calculated for various compounds in all sensors. Using this data, a signature "fingerprint" may be created for each compound. In some instances, this data analysis may be performed, at least in part, via cloud computing. Waypoints for pure chemicals as well as general breath profiles may be stored. For example, a unique breath profile of an individual may be stored in a database, allowing comparisons with laboratory-determined breath profile values in order to make conclusions as to a diagnosis. The breath profile may be generated for an individual or as a general breath profile for a condition. Accordingly, using the breath profile, a simple diagnosis for a given condition may be generated by analyzing the breath of an individual. Diagnostic profiles can currently be loaded and duplicated on all sensor arrays comprised of the same sensors. When the creation of a new diagnostic profile is desired, the procedure is repeated.

For example, multiple biomarker VOCs indicative of the level of drowsiness expressed by an individual may be identified. Concurrently, calibration curves may be experimentally determined in order to detect signal changes in response to various biomarkers with different sensors within the sensor array. Ultimately, a library of signal responses to a drowsy individuals' breath may be generated. After producing the calibration curves, human studies may be performed to identify the changes in biomarker signaling exhibited by drowsy individuals in a suitably equivalent testing environment, i.e. a driving simulator. Various medical conditions known to exhibit VOC profile changes may be tested in a similar way, to develop libraries of signal responses to individuals' breath based on other medical conditions.

In a vehicular environment, sensors may be placed at various locations in the vehicle to achieve different effects on sample sensitivity as well as temporal sensitivity. For example, sensors may be placed in particular locations within the vehicle to accurately determine detected VOC biomarkers are from a driver or are being produced by other occupants. Of course, the use of these sensors within a vehicle is just one example of the technology described herein. The systems and methods described herein may be used in many other medical situations from rural health care to mobile healthcare to fast trauma diagnosis and use in hospitals.

Figure 6:
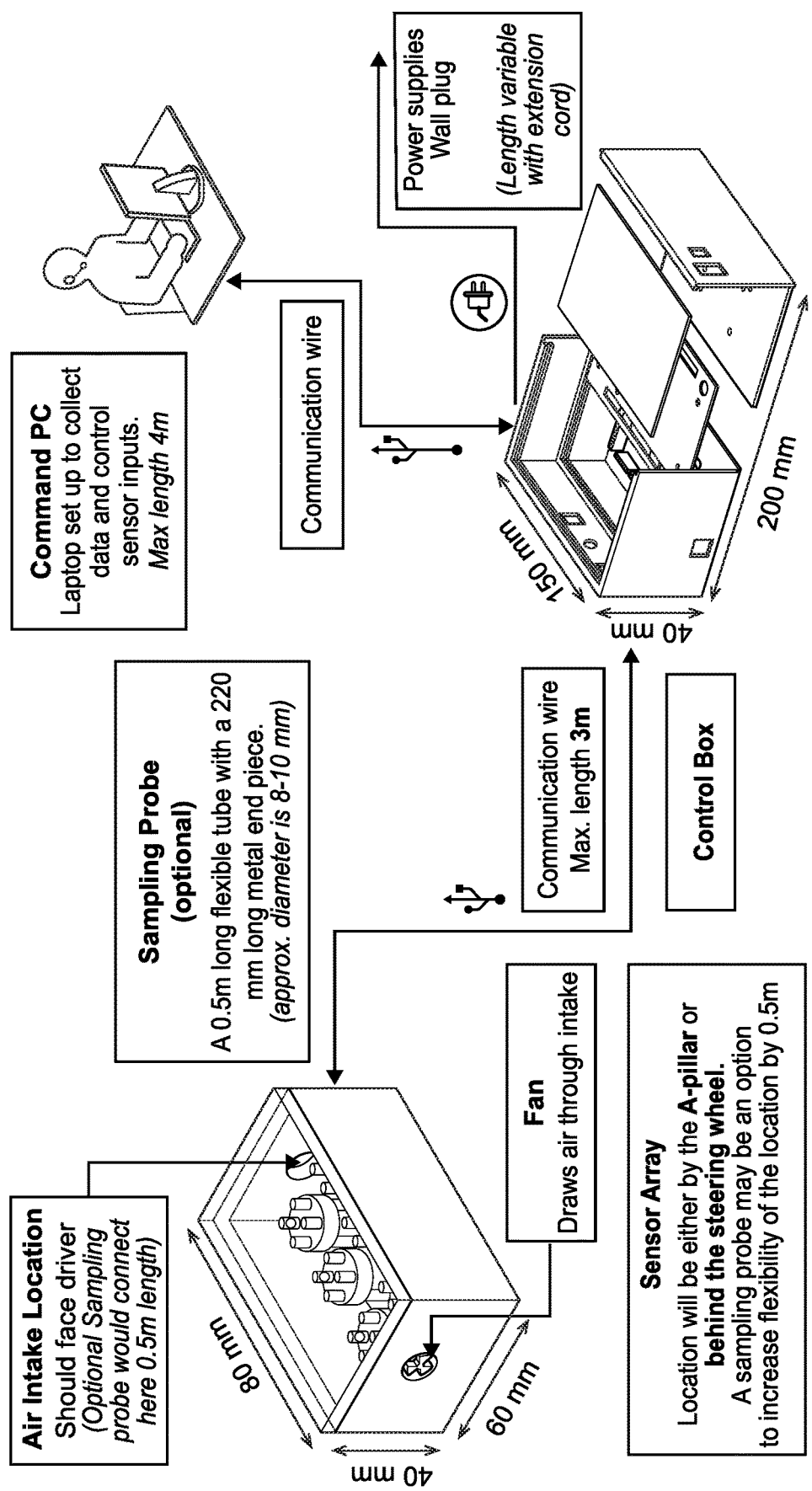
FIG. 6 illustrates an exemplary solid-state sensor array setup within a vehicle, in accordance with an embodiment.
Figure 7:
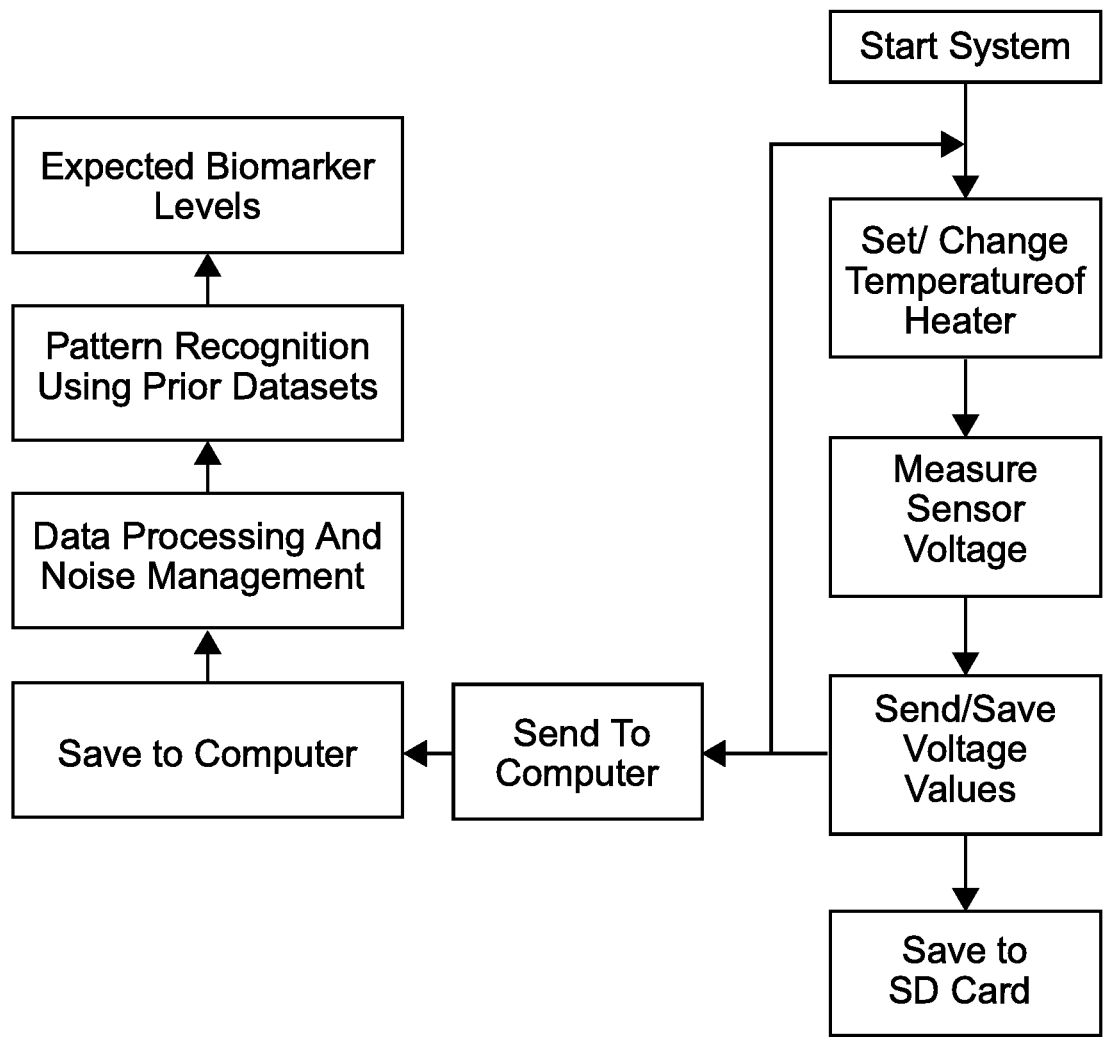
FIG. 7 illustrates an exemplary method for detecting a condition in an individual by analyzing the individual's breath using solid-state sensors, in accordance with an embodiment

As shown in FIG. 6, an exemplary sensor setup within a vehicle may include a sensor array positioned, e.g., near the A-pillar or behind the steering wheel. The sensor array may include several solid-state sensors, an opening for air intake, and a fan to draw air into the intake opening. In some instances, the sensor array may further include a pump (not shown) to draw air into the intake opening. Accordingly, the solid-state sensors will be exposed to air from within the vehicle (including VOCs present in the breath of the vehicle driver). In some instance, the sensor array may further include a sampling probe. The sensor array may be communicatively connected to a computing device (e.g., the command PC shown in FIG. 6), which may include any number of memories and/or processors configured to analyze the data captured by the solid-state sensors (such as, e.g., resistance and/or voltage measurements). The command PC may analyze data captured by the solid-state sensors in real time. In some instances, this data analysis may be performed, at least in part, via cloud computing. FIG. 7 illustrates an exemplary method for detecting a condition in an individual by analyzing the individual's breath using solid-state sensors, e.g., using the setup shown in FIG. 6. As shown in FIG. 7, a heater may be set to a given temperature, and the sensor voltage may be measured and saved. This process may be repeated several times at various temperatures. The saved sensor voltages may then be processed (e.g., including filtering out of noise) to identify patterns related to particular biomarkers. In some instances, the biomarkers may then be matched to conditions associated with each biomarker, such as, e.g., drowsiness, or other medical conditions. In some instances, this data analysis may be performed, at least in part, via cloud computing.

Advantageously, non-invasive real-time monitoring with solid-state sensor arrays may greatly improve the speed at which health personnel make diagnoses and thereafter implement treatment—thus increasing the chances of speedy and full recovery. Moreover, as an additional advantage, solid-state sensor arrays may detect biomarkers before the first symptom is observed by an individual, thus making treatment much faster with fewer complications. That is, most current diagnostic procedures take place only when the patient is severely afflicted enough that a doctor's visit is required. By comparison, by using solid-state sensor arrays to detect biomarker VOCs indicative of various medical conditions, these medical conditions may be detected early on, e.g., during routine checkups.

Furthermore, using solid-state sensor arrays to detect biomarker VOCs indicative of various medical conditions may save medical resources. For instance, while currently a doctor may order a number of expensive tests involving laboratory personnel in order to pinpoint the cause of a patent's illness (especially those bearing a number of general symptoms), the technology described herein allows a doctor to simply use a single quick and inexpensive test. This is not to mention the amount of time that it takes for test results to return, during which a patient's condition may deteriorate further—especially if medications for the wrong illness were administered. Moreover, the simplicity of these biomarker detection tests also allows for less-specialized medical personnel to administer them, allowing for more specialized personnel to be reserved for more demanding tasks. Overall, this development stands to significantly improve patient experience by allowing fewer side effects, lower costs and less follow-up visits.

For quality improvement on breath sampling and analysis techniques, a pilot study was completed using human subjects pre- and post-24-hour shift. The pilot study revealed a correlation between VOC profile changes and drowsiness of individuals who slept six hours on average before and 1.5 hours on average after a 24-hour shift. A cohort of surgical residents who were performing "night-shift" duties for testing of drowsiness and fatigue were used for the pilot study and are involved in the ongoing 100-subject study with full protocol. The full protocol utilized medically accepted sleep surveys and tests to analyze and measure the amount of drowsiness present.

Figure 8:
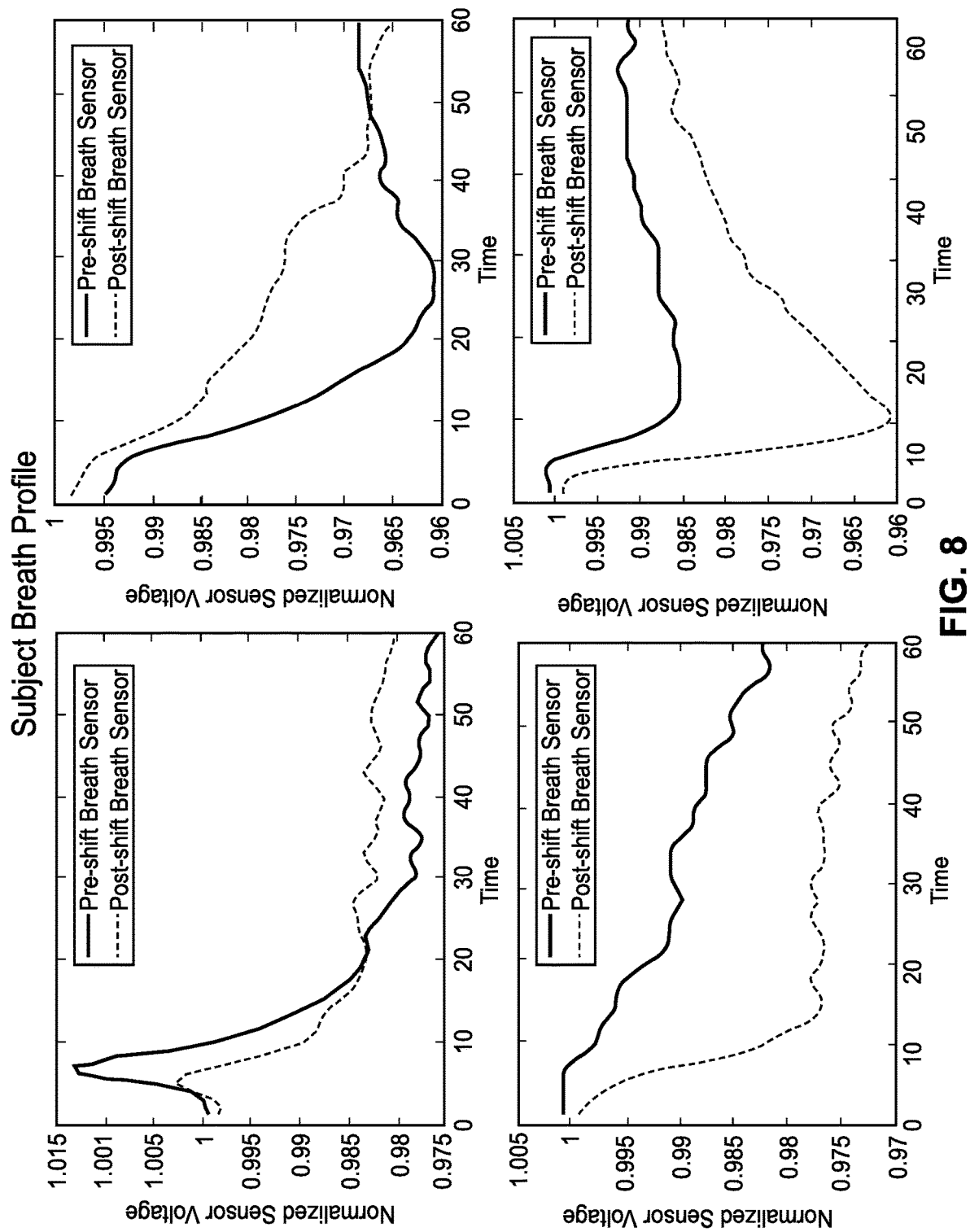
FIG. 8 illustrates the normalized response of biomarker sensors to subject's breath pre- and post-24-hour work shift, in a lab setting, in accordance with an embodiment.
Figure 9:
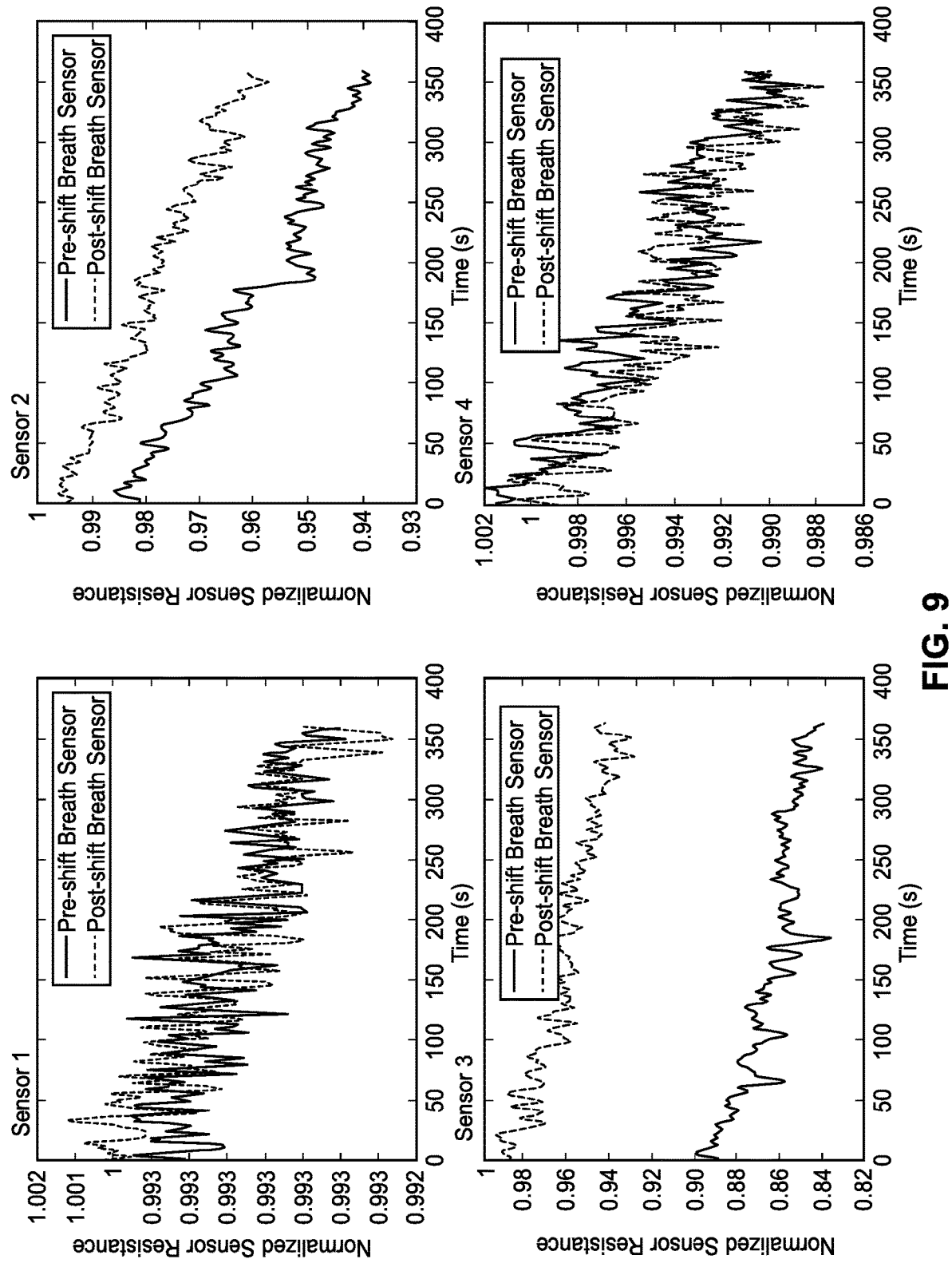
FIG. 9 illustrates the normalized response of biomarker sensors to the subject's breath pre- and post-24-hour work shift, in a vehicle setting, in accordance with an embodiment.

The breath sample and survey data were collected from the participants before and after their 24-hour night shift. The number of hours of sleep and participants' self-reported level of alertness are recorded before and after their shift. The results of the study are shown in FIGS. 8 and 9. Specifically, FIG. 8 illustrates the normalized response of biomarker sensors to subject's breath pre- and post-24-hour work shift, in a lab setting, while FIG. 9 illustrates the normalized response of biomarker sensors to the subject's breath pre- and post-24-hour work shift in a vehicle setting. As shown in FIG. 8, the sensors in the lab environment produce markedly different signals in response to the overall breath profile change after the 24-hour work shift. As shown in FIG. 9, the sensors in the vehicle environment also produce markedly different signals in response to the overall breath profile change after the 24-hour work shift.

The levels detected when rested and fatigued were compared and analyzed for correlation with the breath VOC profiles measured. Both stress and drowsiness/fatigue were primary targets for this study. Target molecule identification is underway and will increase diagnosis accuracy and precision, but correlation alone has already proven effective as a potential identifier of drowsiness by itself. This correlation between the VOC profile without actual biomarker being known will prove valuable for identification and diagnosis for new conditions in the future. Based on what is known in the literature, human subjects in both stressed states and sleep-deprived states were chosen to identify target molecules to be measured. The literature shows many other medical conditions where breath analysis could be useful, and superior compared to current techniques.

Figure 10A:
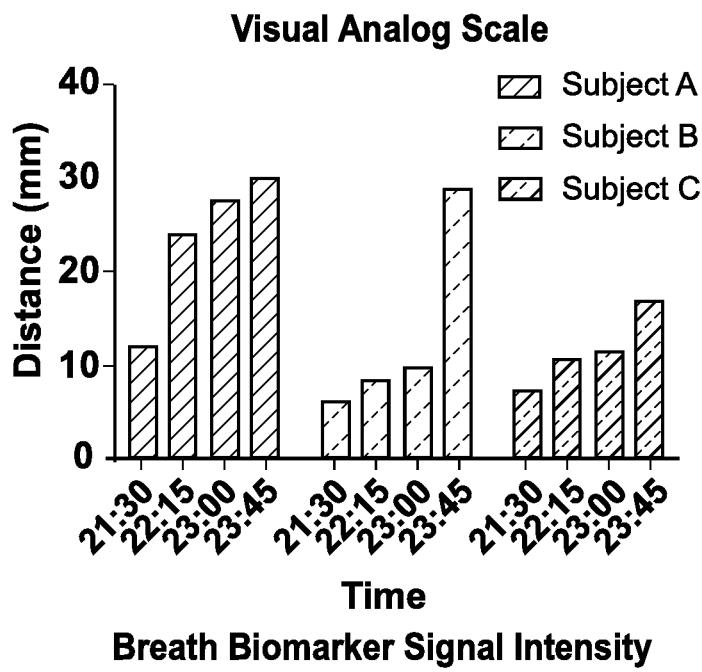
FIGS. 10A-10C illustrate the results of a study analyzing the breath of volunteers after an eight-hour shift, in accordance with an embodiment.
Figure 10B:
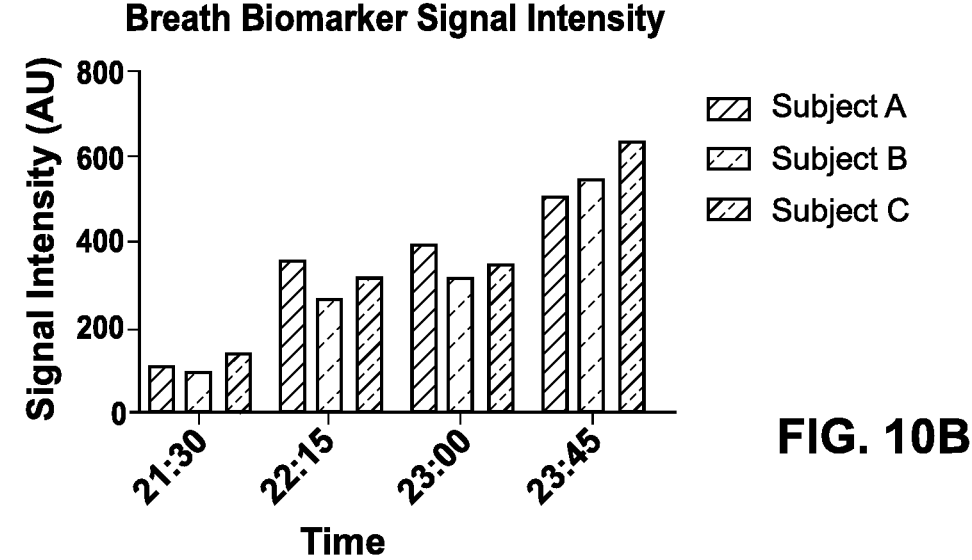
Figure 10C:
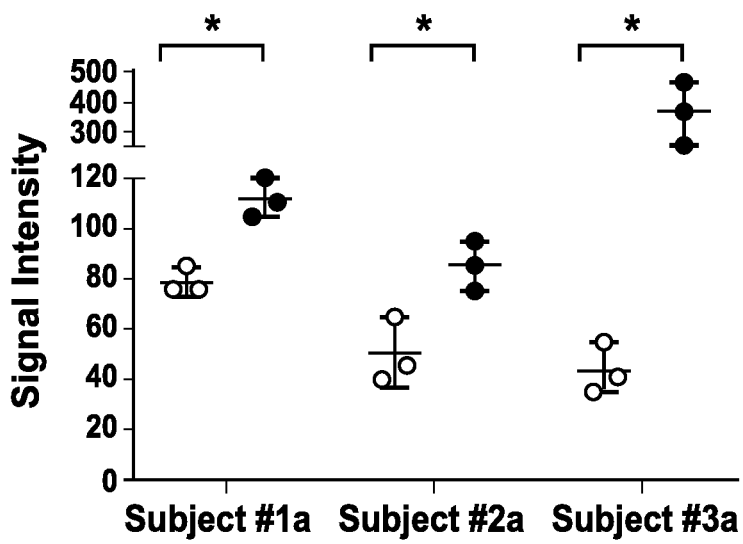

An additional study was completed, analyzing the breath of volunteers after an eight-hour shift to create a biomarker detection scenario comparable to an individual having just left work and driving. The subjects' diets were controlled so that any variation from food was comparable. The three subjects were monitored at 45-minute intervals. The breath samples were collected in Tedlar bags which were later used for sampling with the sampling probe. These results were compared to the benchmarks of the Karolinska Sleepiness Scale. The results of this study are illustrated in FIGS. 10A-10C.

The participants in the sleep study were given a response card with a line on it containing no units, only verbiage indicating "not sleepy" on one end of the line and "sleepy" on the other end of the line. The participants were asked to rate their drowsiness by placing a notch on the line. To ensure that previous responses do not affect a response, subjects are not allowed to see their previous responses. The line was 100 millimeters long, and the distance of the notch from the beginning of the line is measured to give the response in millimeters. As participants are tested at later and later times, FIG. 10A shows that the distance at which the notch is placed on the scale continues to increase—signifying that the subjects continue to feel more and more drowsy as time goes by. As shown in FIG. 10B, an increase was observed in the biomarker activity of the breath profiles of the individuals as time passed. As shown in FIG. 10C, the breath analysis showed statistical significance when analyzing breath repeatedly of same individuals before and after 24-hour shift. These results also correlated well with the reported levels of sleepiness on the Karolinska Sleepiness Scale (KSS). This test was to demonstrate that the biomarkers detected by the solid-state sensors were well-correlated with sleepiness index from a well-established instrument.

Figure 11:
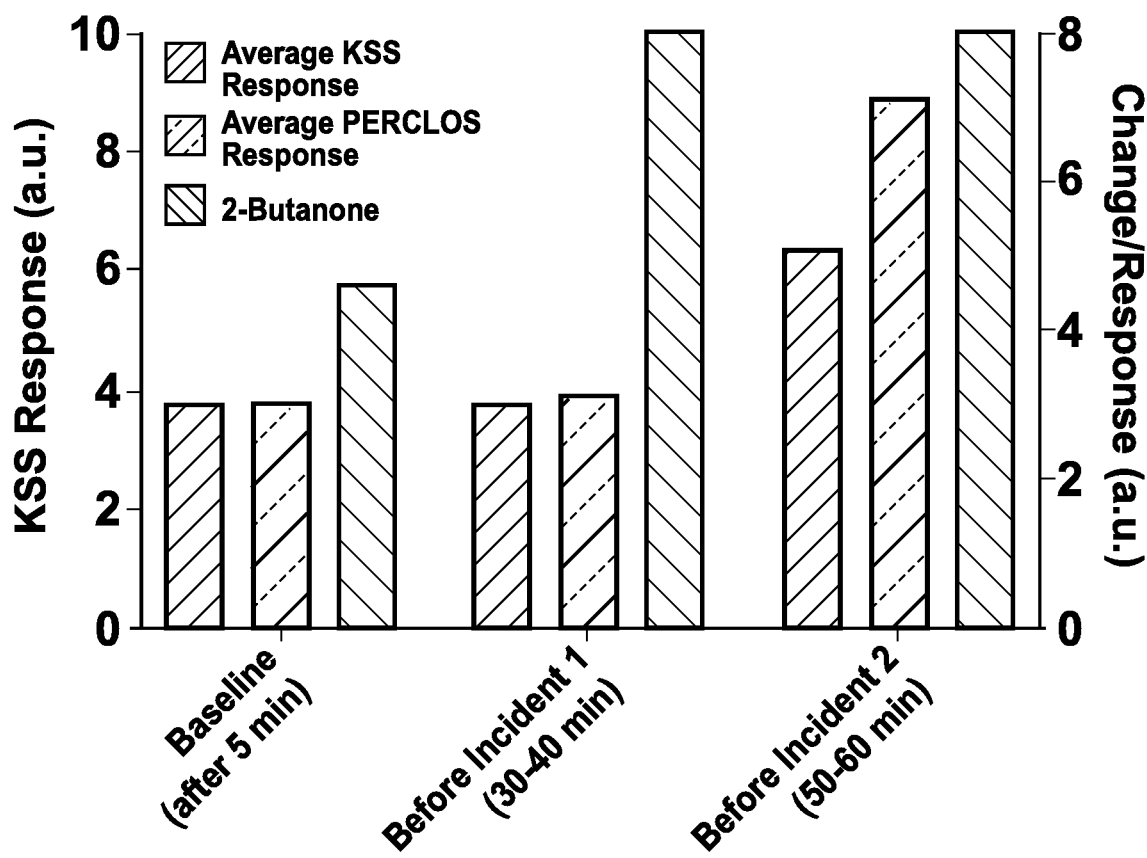
FIG. 11 illustrates a bar graph showing the results of a study in which Karolinska Sleepiness Scale (KSS), percentage of eye closure (PERCLOS) and sensor responses were measured for subjects during simulated driving after performing fatigue-inducing tasks, in accordance with an embodiment.

Moreover, another study was completed, in which KSS, percentage of eye closure (PERCLOS) and biomarker sensor responses for 2-butanone were measured for subjects during simulated driving after performing fatigue-inducing tasks. Specifically, the KSS, PERCLOS and biomarker sensor responses for 2-Butanone were measured before and after two driving accident simulations ("incident 1" and "incident 2"). The results of this study are illustrated in FIG. 11. In particular, the bar graph shown in FIG. 11 suggests that the 2-butanone sensor response is well correlated with the other accepted physiological metrics of fatigue and drowsiness.

Figure 12:
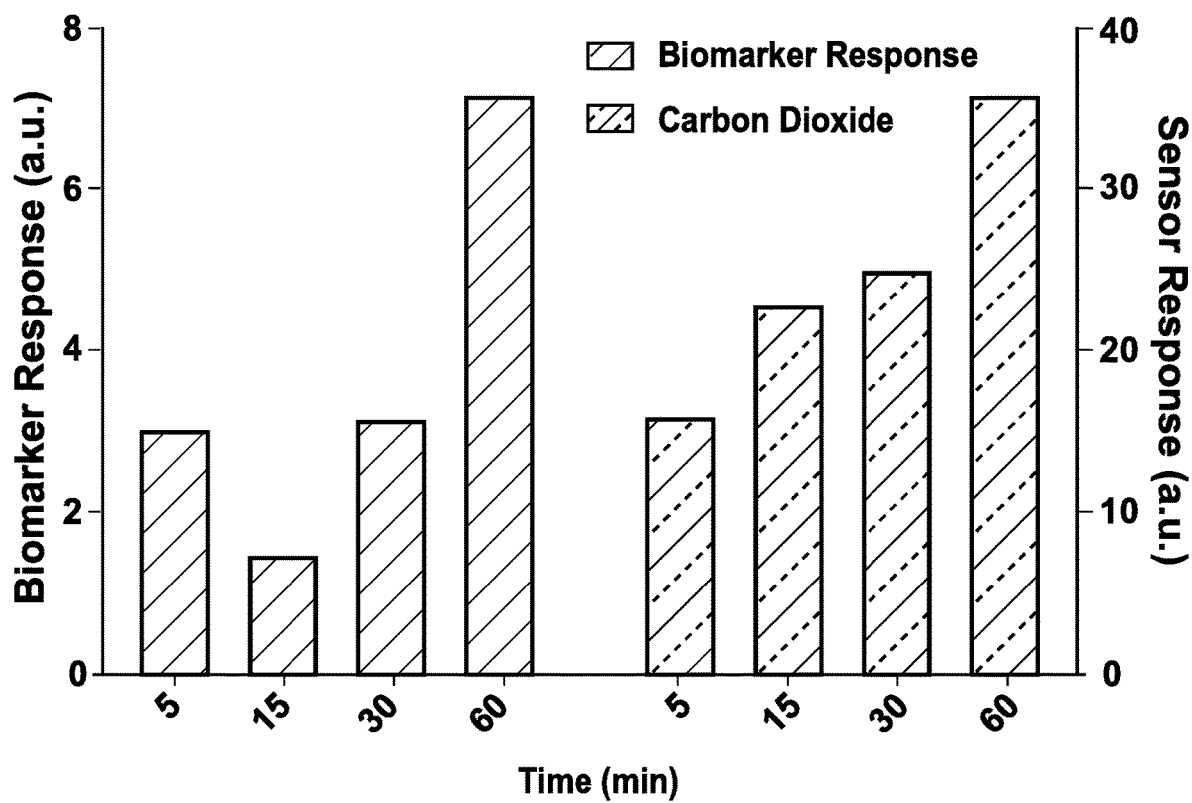
FIG. 12 illustrates a bar graph showing the results of a study in which sensor responses to a biomarker for fatigue and to carbon dioxide were each measured over time as subjects used a driving simulator in a vehicle, in accordance with an embodiment.

Additionally, another study was completed, in which sensor responses to a biomarker sensor responses for 2-butanone and to carbon dioxide were each measured over time as subjects used a 3-D augmented reality driving simulator in a vehicle. FIG. 12 illustrates the results of that study. In particular, as shown in FIG. 12, the response of the state sensor suggests that the average biomarker response in subjects increased after being in the vehicle for a longer time, while the carbon dioxide sensor confirmed the presence of the occupant in the vehicle.

Figure 13A:
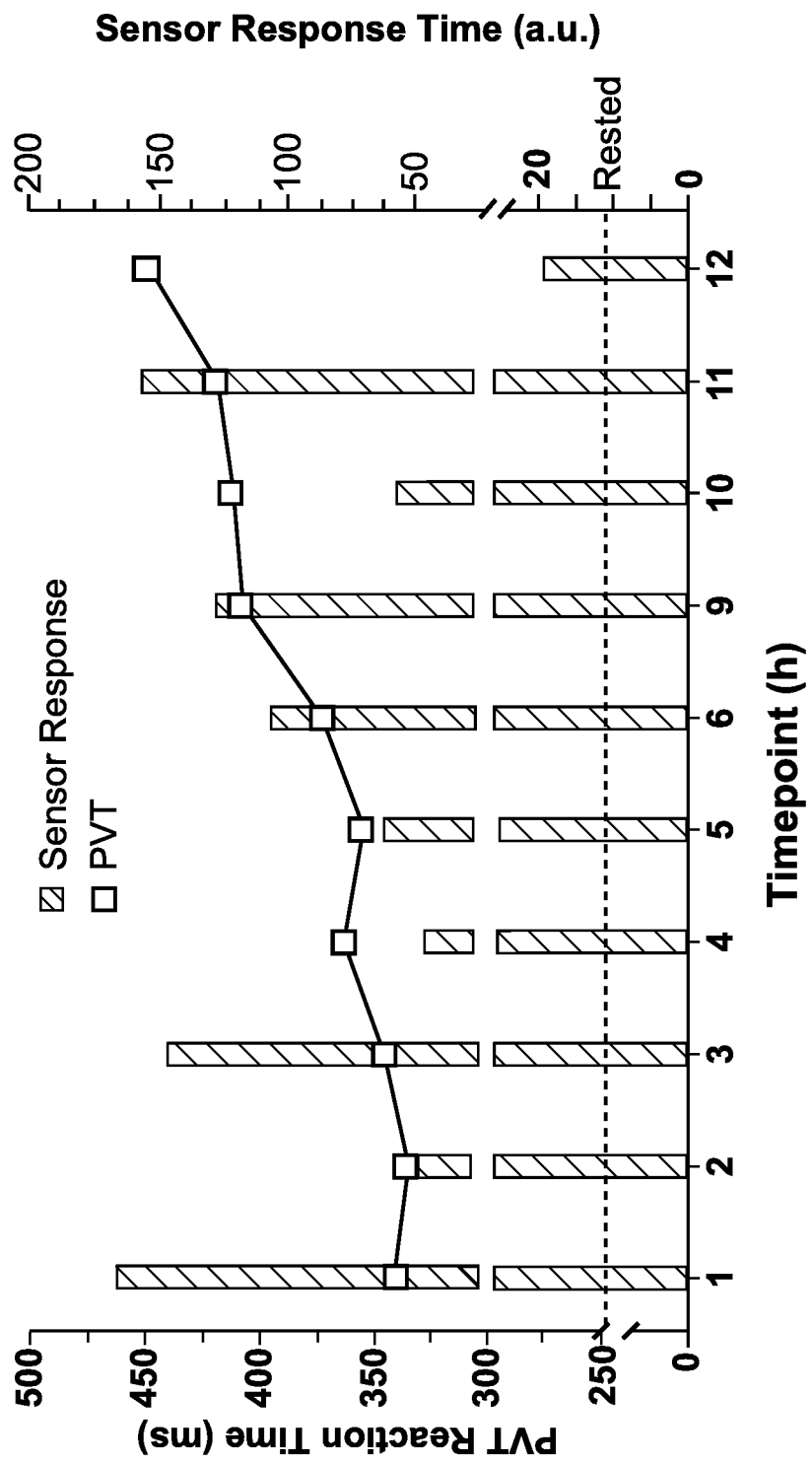
FIGS. 13A-13C illustrate the results of a study in which biomarker sensor and psychomotor vigilance test (PVT) responses were measured for subjects staying up awake for an additional 12 hours after a work shift, in accordance with an embodiment.
Figure 13B:
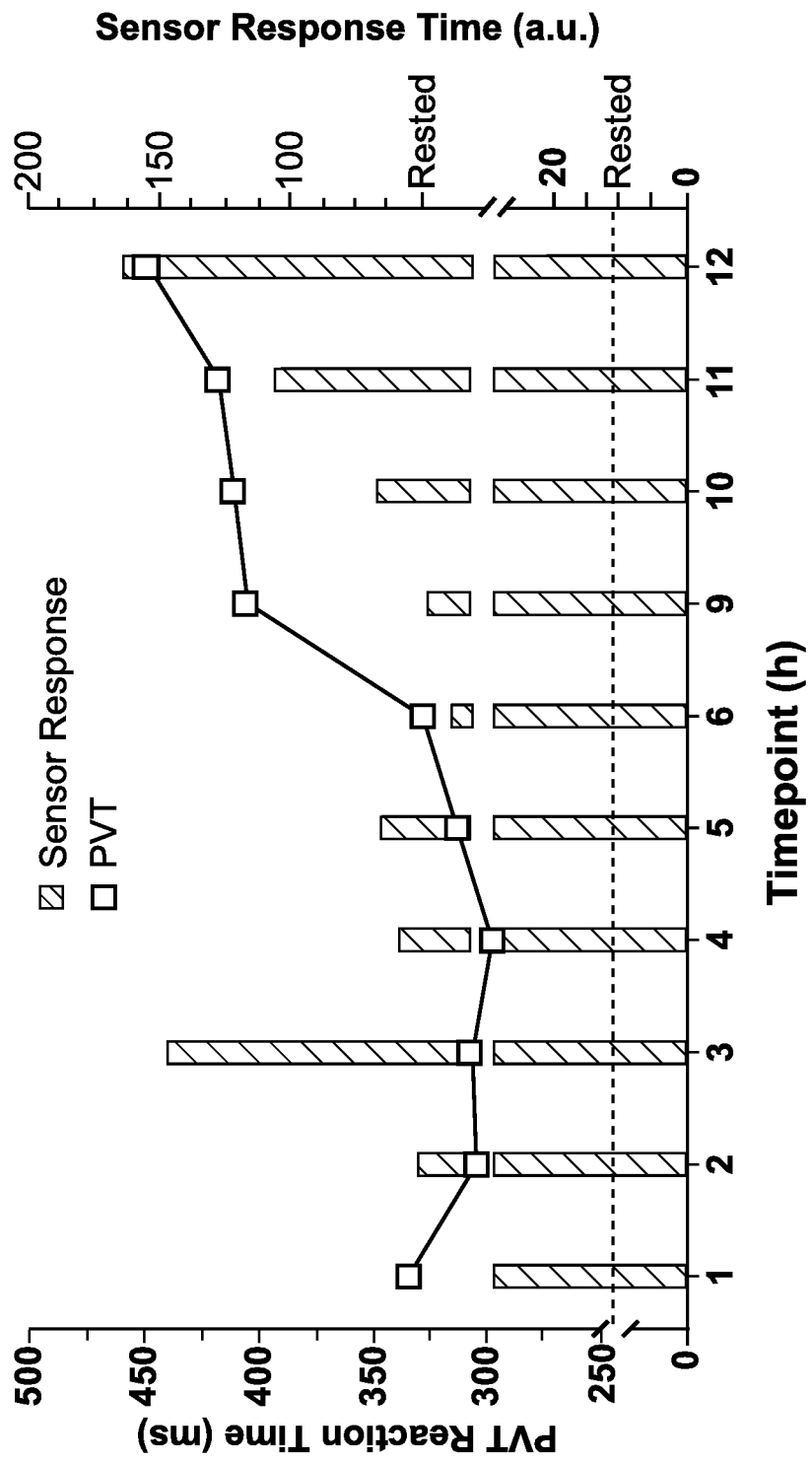
Figure 13C:
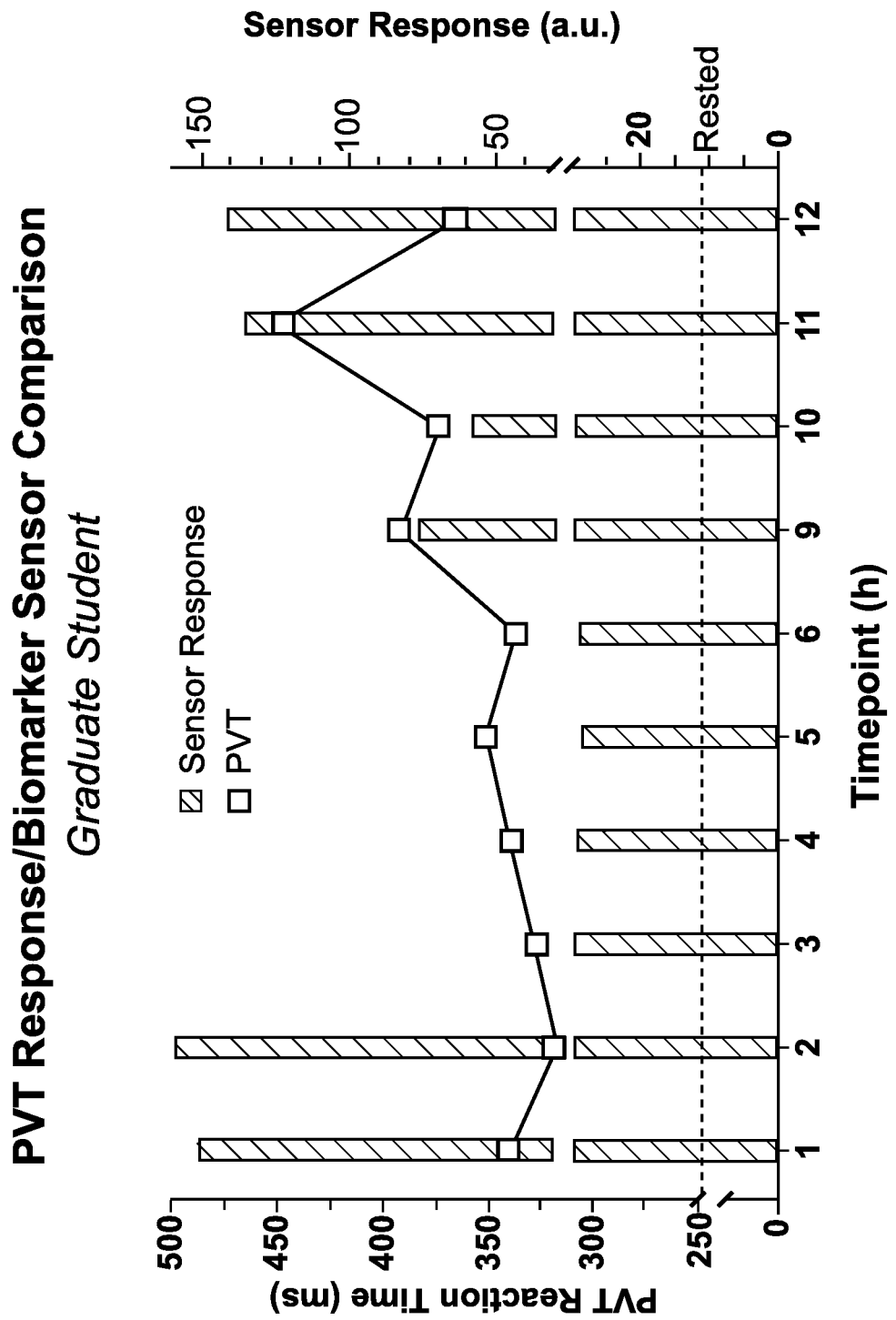

Furthermore, another study was completed, in which biomarker sensor responses for 2-butanone and psychomotor vigilance test (PVT) responses were measured for various different subjects who remained awake for an additional 12 hours after their respective work shifts. FIGS. 13A-13C illustrate the results of that study. In particular, as shown in FIGS. 13A-13C, the PVT reaction time increases as the number of hours awake increases, i.e., the PVT reaction time shows a positive correlation with the number of hours the subject stayed awake. Moreover, as shown in FIGS. 13A-13C, the biomarker sensor response was well above the rested baseline (dotted line) which suggests that the biomarker concentration was already high after the initial work shift.

Figure 14:
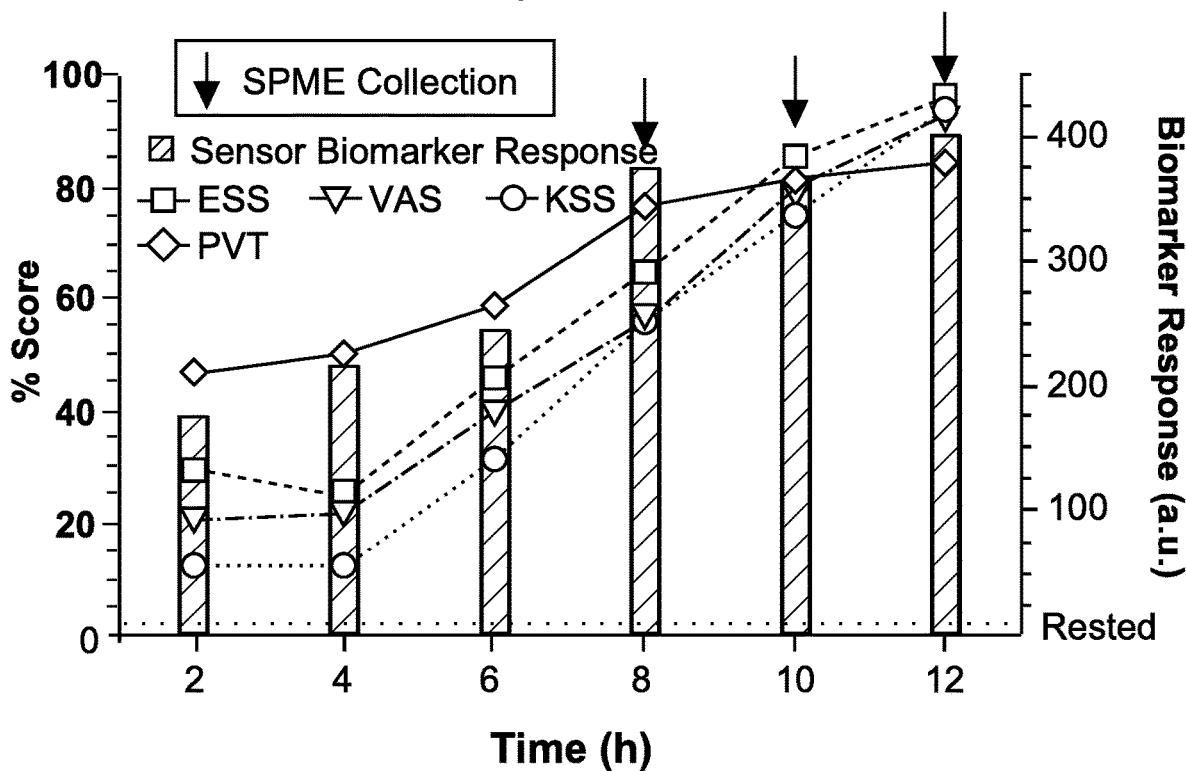
FIG. 14 illustrates the results of a study in which subjects' biomarker responses were measured as a variety of recognized drowsiness tests (including the Epworth Sleepiness Scale (ESS), PVT, and KSS) were performed on the subjects, in accordance with an embodiment.

Moreover, another study was performed, in which subjects' biomarker sensor responses for 2-butanone were measured as a variety of recognized drowsiness tests (including Epworth Sleepiness Scale (ESS), PVT, and KSS) were performed on the subjects. FIG. 14 illustrates the results of this study. In particular, it is clear that the results of the recognized drowsiness tests (scored on a scale of 0% to 100%, with higher percentages indicating increased drowsiness) are positively correlated with the subjects' biomarker responses. Additionally, SPME fibers were used in conjunction with Tedlar bags to confirm the 2-butanone biomarkers found in breath and identify potential new biomarkers. The table shown in FIG. 15 illustrates the subset of the various biomarkers identified using SPME fibers and GC-MS. In particular, the left side of the table of FIG. 15 illustrates a listing of previously-identified biomarkers whose presence was confirmed using the SPME fibers used in conjunction with the Tedlar bags, while the right side of the table of FIG. 15 illustrates a listing of new biomarkers identified using the SPME fibers in conjunction with the Tedlar bags.

Figure 16:
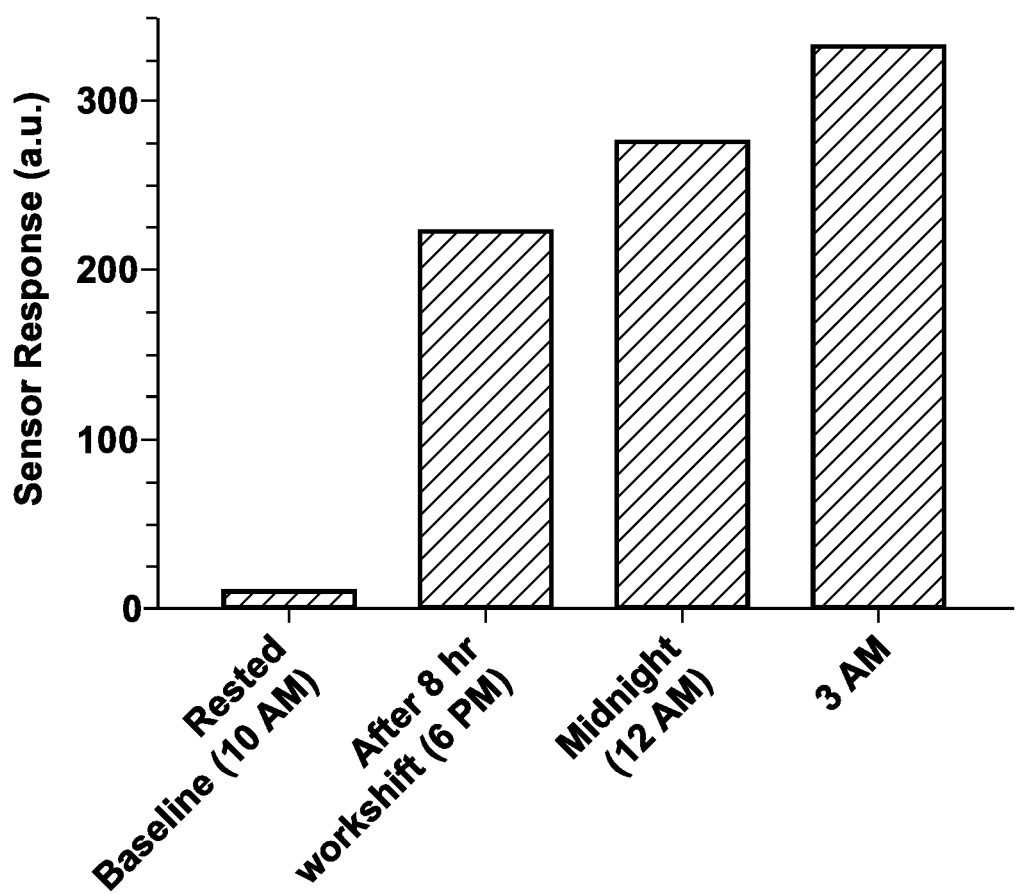
FIG. 16 illustrates the results of a study in which a biomarker sensor response was measured for subjects at various intervals after their normal wake times, in accordance with an embodiment.

Additionally, another study was completed, in which biomarker sensor responses for 2-Butanone was measured for subjects at different intervals after their normal wake times. In this study, the subjects each had a work shift starting between 8:00 AM and 9:00 AM and ending between 5:00 PM and 6:00 PM. FIG. 16 illustrates the averaged biomarker sensor responses from the subjects at each interval. In particular, as shown in FIG. 16, the average biomarker sensor response after the subjects' work shifts (6:00 PM) were significantly different from the rested baseline (10:00 AM). In addition, it can be seen that the average biomarker response increases with time as the individuals stay awake longer.

Figure 17:
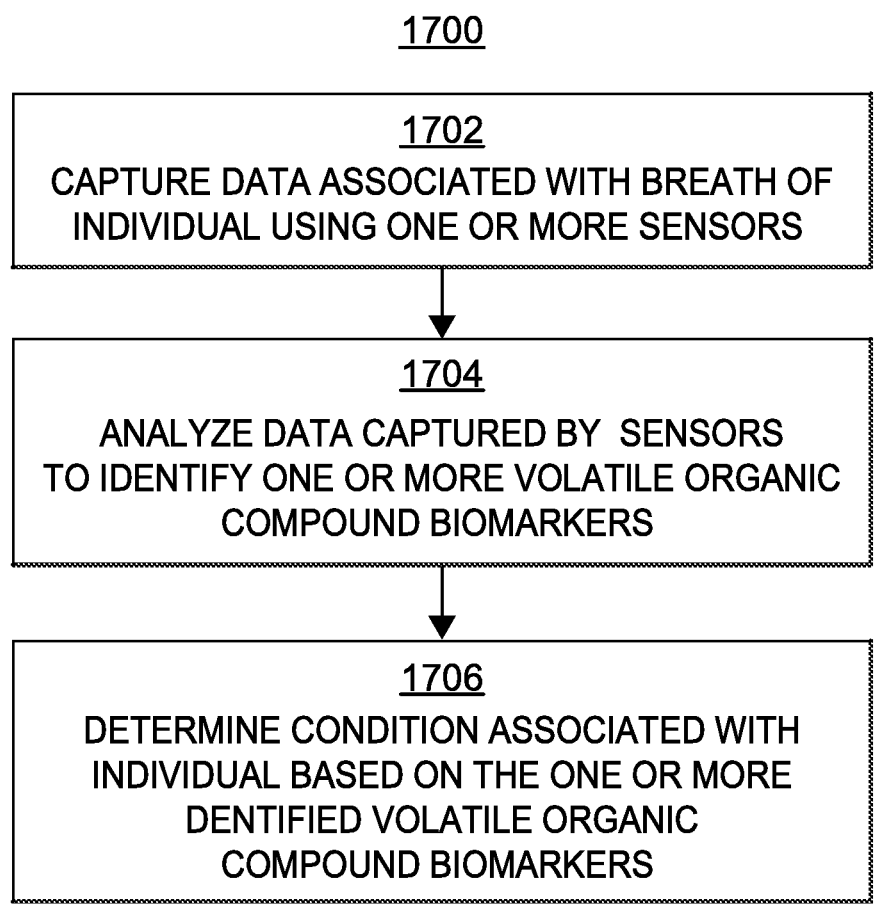
FIG. 17 illustrates a flow diagram of an example method for detecting a condition in an individual by analyzing the individual's breath, in accordance with some embodiments.

FIG. 17 illustrates a flow diagram of an example method 1700 for detecting a condition in an individual by analyzing the individual's breath, in accordance with some embodiments. One or more steps of the method 1700 may be implemented as a set of instructions stored on a computer-readable memory and executable on one or more processors.

At block 1702, data associated with the breath of an individual may be captured using one or more sensors (e.g., solid-state sensors). In some instances, the one or more sensors may together comprise a sensor array ("sensors" and "sensor array" may be used interchangeably herein). Moreover, the sensors may be positioned inside of a vehicle associated with the individual (e.g., to capture data associated with the breath of the individual before, during, or after driving). Capturing the data associated with the breath of the individual using the sensors may include generating heat by a heater associated with the sensors, exposing the sensors to the breath of the individual, and measuring a resistance detected by the sensors while the sensors are exposed to the breath of the individual. In some examples, the resistance may be measured and recorded at various points after modifying the heat generated by the heater associated with the sensors.

At block 1704, the data captured by the one or more sensors may be analyzed, e.g., by a processor, to identify one or more volatile organic compound biomarkers. For instance, the identified biomarkers may include one or more of: 2-Butanone, 4,6-Dimethyldodecane, 2-Methylpentadecane, Ethylhexanes, 2-Ethylhexanol, 1,3-Butylene Glycol, 4-Hydroxy-2-Butanone, Indole, Benzophenone, Hydroxyacetophenone, 1,3-bis(1,1-dimethylethyl)benzene, Phenol, Benzaldehyde, Limonene, 2-ethyl-1-hexanol, 2-exothyethanol, branched long-chain hydrocarbons, 2-methylbutane, 1,4-dioxane, 4-methyl-1-pentanol, 2-methyl-2-butenal, 4-methyloctane, or any other suitable biomarkers associated with medical conditions or drowsiness conditions.

In some examples, a known breath profile associated with the individual may be compared to the captured data associated with the breath of the individual to identify volatile organic compound biomarkers that aren't typically present in the breath of the individual.

At block 1706, a condition associated with the individual may be determined, e.g., by a processor, based on the identified one or more volatile organic compound biomarkers and/or based on the comparison to the individual's typical breath profile. For instance, the condition may be a medical condition, or may be a condition such as drowsiness.

Figure 18:
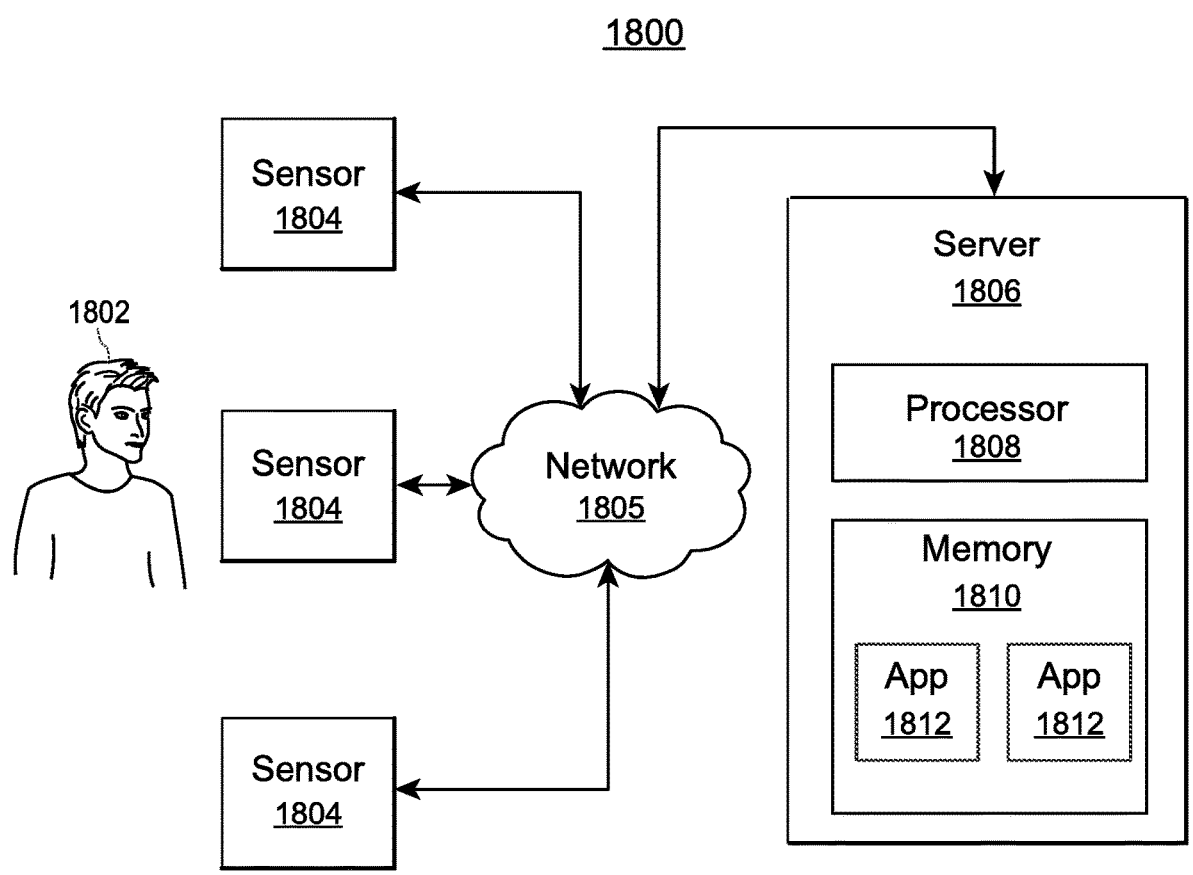
FIG. 18 illustrates a block diagram of an exemplary system for detecting a condition in an individual by analyzing the individual's breath, in accordance with some embodiments.

FIG. 18 illustrates a block diagram of an exemplary system 1800 for detecting a condition in an individual by analyzing the individual's breath, in accordance with some embodiments. As shown in FIG. 18, one or more sensors 1804 (e.g., solid-state sensors) may capture data associated with the breath of an individual 1802. The sensors 1804 may communicate the captured data to a server 1806 (e.g., via a network 1805). The server 1806 may include one or more processors 1808 and a memory 1810. The processors 1808 may include, for example, one or more microprocessors, controllers, and/or any suitable type of processor. The memory 1810 (e.g., volatile memory, non-volatile memory) may be accessible by the one or more processors 1808 (e.g., via a memory controller). The one or more processors 1808 may interact with the memory 1810 to obtain, for example, machine-readable instructions stored in the memory 1808. Additionally or alternatively, machine-readable instructions may be stored on one or more removable media (e.g., a compact disc, a digital versatile disc, removable flash memory, etc.) that may be coupled to the server 1806 to provide access to the machine-readable instructions stored thereon. In particular, the machine-readable instructions stored on the memory 1808 may include one or more applications 1812 for carrying out any of the steps of any of the methods described in greater detail above with respect to FIG. 17.

As shown in the figures, "A.U." refers to "arbitrary units."

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed is:

1. A method for detecting a condition in an individual by analyzing the individual's breath, the method comprising:
    capturing, by one or more sensors, data associated with the breath of the individual, wherein capturing the data associated with the breath of the individual comprises:
        generating heat by a heater associated with the one or more sensors while the one or more sensors are exposed to the breath of the individual;
        measuring a first resistance detected by the one or more sensors while the one or more sensors are exposed to the breath of the individual;
        modifying the heat generated by the heater associated with the one or more sensors while the one or more sensors are exposed to the breath of the individual, after measuring the first resistance; and
        measuring a second resistance detected by the one or more sensors while the one or more sensors are exposed to the breath of the individual, after modifying the heat generated by the heater;
    analyzing, by a processor, the data captured by the one or more sensors to identify one or more volatile organic compound biomarkers; and
    determining, by the processor, based on the identified one or more volatile organic compound biomarkers, a condition associated with the individual.

2. The method of claim 1, wherein the one or more sensors are solid-state sensors.

3. The method of claim 1, wherein the one or more sensors are included in a sensor array.

4. The method of claim 1, wherein the one or more sensors are positioned inside of a vehicle associated with the individual.

5. The method of claim 1, wherein determining the condition associated with the individual comprises:
    comparing, by the processor, a breath profile associated with the individual to the captured data associated with the breath of the individual to determine the condition associated with the individual.

6. The method of claim 1, wherein the condition associated with the individual is a medical condition.

7. The method of claim 1, wherein the condition associated with the individual is a drowsiness condition.

8. The method of claim 7, wherein the identified one or more volatile organic compound biomarkers include one or more of:
    2-Butanone,
    4,6-Dimethyldodecane,
    2-Methylpentadecane,
    Ethylhexanes,
    2-Ethylhexanol,
    1,3-Butylene Glycol,
    4-Hydroxy-2-Butanone,
    Indole,
    Benzophenone,
    Hydroxyacetophenone,
    1,3-bis(1,1-dimethylethyl)benzene,
    Phenol,
    Benzaldehyde, and/or
    Limonene.

9. A system for detecting a condition in an individual by analyzing the individual's breath, the system comprising:
    one or more sensors configured to capture data associated with the breath of the individual;
    a heater associated with the one or more sensors configured to generate heat while the one or more sensors are exposed to the breath of the individual;
    a memory having stored thereon computer executable instructions; and
    at least one processor configured to interface with the one or more sensors, the heater, and the memory, and configured to execute the computer executable instructions to cause the at least one processor to:
        cause the heater associated with the one or more sensors to generate heat while the one or more sensors are exposed to the breath of the individual;

cause the one or more sensors to measure a first resistance while the one or more sensors are exposed to the breath of the individual;
cause the heater to modify the heat generated by the heater while the one or more sensors are exposed to the breath of the individual, after measuring the first resistance; and
cause the one or more sensors to measure a second resistance while the one or more sensors are exposed to the breath of the individual, after modifying the heat generated by the heater;
analyze the data captured by the one or more sensors to identify one or more volatile organic compound biomarkers; and
determine, based on the identified one or more volatile organic compound biomarkers, a condition associated with the individual.

10. The system of claim 9, wherein analyzing the data captured by the one or more sensors to identify the one or more volatile organic compound biomarkers includes analyzing the data via cloud computing.

11. The system of claim 9, wherein the one or more sensors are solid-state sensors.

12. The system of claim 9, wherein the one or more sensors are included in a sensor array.

13. The system of claim 9, wherein the one or more sensors are positioned inside of a vehicle associated with the individual.

14. The system of claim 9, wherein the computer executable instructions cause the at least one processor to determine the condition associated with the individual by comparing a breath profile associated with the individual to the captured data associated with the breath of the individual to determine the condition associated with the individual.

15. The system of claim 9, wherein the condition associated with the individual is one or more of a medical condition or a drowsiness condition.

16. The system of claim 15, wherein the identified one or more volatile organic compound biomarkers include one or more of:
2-Butanone,
4,6-Dimethyldodecane,
2-Methylpentadecane,
Ethylhexanes,
2-Ethylhexanol,
1,3-Butylene Glycol,
4-Hydroxy-2-Butanone,
Indole,
Benzophenone,
Hydroxyacetophenone,
1,3-bis(1,1-dimethylethyl)benzene,
Phenol,
Benzaldehyde, and/or
Limonene.

* * * * *

UNITED STATES PATENT AND TRADEMARK OFFICE
CERTIFICATE OF CORRECTION

| | |
|---|---|
| PATENT NO. | : 11,850,035 B2 |
| APPLICATION NO. | : 15/733998 |
| DATED | : December 26, 2023 |
| INVENTOR(S) | : Sylvia Daunert et al. |

It is certified that error appears in the above-identified patent and that said Letters Patent is hereby corrected as shown below:

In the Claims

At Column 11, Line 7, "resistance; and" should be -- resistance; --.

Signed and Sealed this
Twenty-fifth Day of June, 2024

Katherine Kelly Vidal
*Director of the United States Patent and Trademark Office*